US00PP29737P2

(12) United States Plant Patent
Trees

(10) Patent No.: US PP29,737 P2
(45) Date of Patent: Oct. 9, 2018

(54) ***LEUCANTHEMUM* PLANT NAMED 'WHITE MAGIC'**

(50) Latin Name: ***Leucanthemum* x *superbum***
Varietal Denomination: White Magic

(71) Applicant: Sunrise Farm Flowers, LLC, Arroyo Grande, CA (US)

(72) Inventor: Scott C. Trees, Arroyo Grande, CA (US)

(73) Assignee: Sunrise Farm Flowers, LLC, Arroyo Grande, CA (US)

( * ) Notice: Subject to any disclaimer, the term of this patent is extended or adjusted under 35 U.S.C. 154(b) by 0 days.

(21) Appl. No.: 15/731,891

(22) Filed: Aug. 21, 2017

(51) Int. Cl.
*A01H 5/02* (2018.01)

(52) U.S. Cl.
USPC ..... Plt./285

(58) Field of Classification Search
USPC ..... Plt./285
See application file for complete search history.

*Primary Examiner* — Susan McCormick Ewoldt
(74) *Attorney, Agent, or Firm* — Audrey Charles

(57) ABSTRACT

A new and distinct cultivar of *Leucanthemum* plant named 'White Magic', characterized by its semi-double type, pure white-colored inflorescences, medium green-colored foliage, moderately vigorous, upright growth habit, is disclosed.

1 Drawing Sheet

Latin name of genus and species of plant claimed: *Leucanthemum* x *superbum.*

Variety denomination: 'White Magic'.

BACKGROUND OF THE INVENTION

The present invention relates to a new and distinct cultivar of *Leucanthemum* plant botanically known as *Leucanthemum* x *superbum* and hereinafter referred to by the cultivar name 'White Magic'.

The new cultivar originated in a controlled breeding program in Arroyo Grande, Calif. during September 2011. The objective of the breeding program was the development of *Leucanthemum* cultivars having a long blooming season that doesn't require deadheading to rebloom.

The new *Leucanthemum* cultivar is the result of open-pollination. The female (seed) parent of the new cultivar is 'Crazy Daisy', not patented, characterized by its semi-to fully double-type, pure white-colored flowers with ray florets having fringed margins, medium green-colored foliage, and vigorous, upright growth habit. The male (pollen) parent of the new cultivar is unknown. The new cultivar was discovered and selected as a single flowering plant within the progeny of the above stated open-pollination during October 2012 in a controlled environment in Arroyo Grande, Calif.

Asexual reproduction of the new cultivar by terminal stem cuttings since October 2012 in Arroyo Grande, Calif. and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'White Magic' as a new and distinct cultivar of *Leucanthemum* plant:

1. Semi-double type, pure white-colored inflorescences;
2. Medium green-colored foliage; and
3. Moderately vigorous, upright growth habit.

Plants of the new cultivar differ from plants of the female parent primarily in having larger diameter inflorescences and ray florets without frilled margins.

Of the many commercially available *Leucanthemum* cultivars, the most similar in comparison to the new cultivar is the *Leucanthemum* cultivar 'Becky', not patented. However, in side by side comparisons, plants of the new cultivar differ from plants of 'Becky' in at least the following characteristics:

1. Plants of the new cultivar have larger diameter inflorescences than plants of 'Becky'; and
2. Plants of the new cultivar are shorter than plants of 'Becky'.

In addition the new cultivar can be compared to REALFLOR 'Real Neat', U.S. Plant Pat. No. 26,185. In comparison plants of the new cultivar differ from plants of 'Real Neat' in at least the following characteristics:

1. Plants of the new cultivar have a ray floret shape different from plants of 'Real Neat';
2. Plants of the new cultivar have larger diameter inflorescences than plants of 'Real Neat'; and
3. Plants of the new cultivar have longer and wider ray florets than plants of 'Real Neat'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'White Magic'. The plants were approximately 16-weeks old and grown in Elburn, Ill. in one-gallon containers for approximately 4 weeks in a greenhouse and 6 weeks outdoors.

DETAILED BOTANICAL DESCRIPTION

Figure 1:
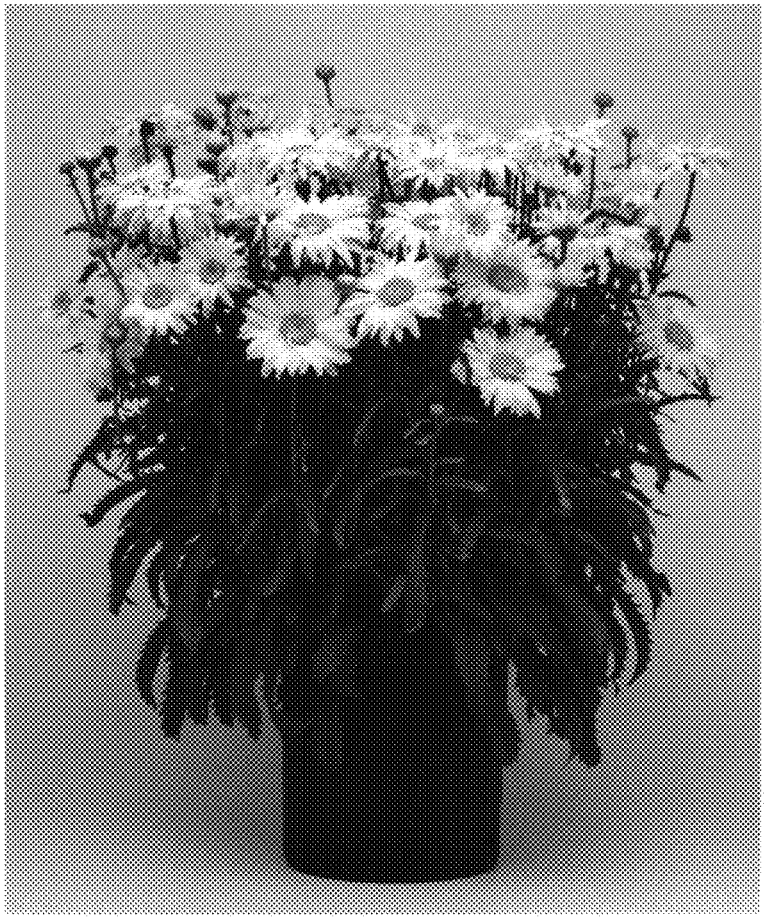
FIG. 1 illustrates a side view of the overall growth and flowering habit of 'White Magic'.
Figure 2:
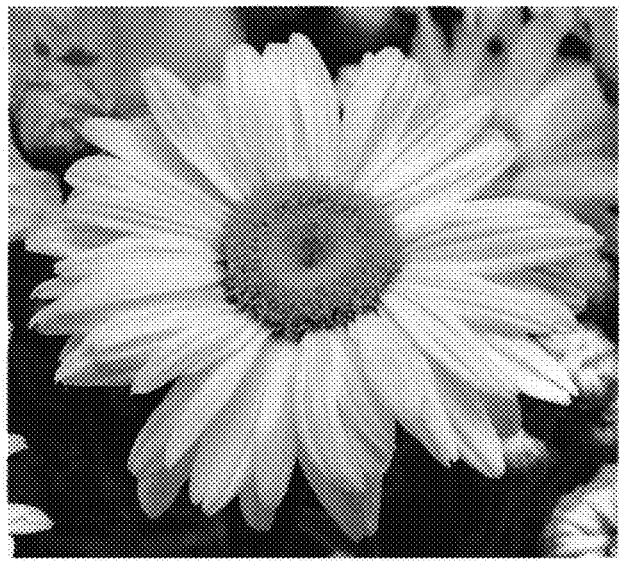
FIG. 2 illustrates a close-up view of an individual inflorescence of 'White Magic'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2017 under natural light conditions in West Chicago, Ill.

The following descriptions and measurements describe approximately 18-week old plants produced from cuttings and grown in a glass-covered greenhouse under conditions comparable to those used in commercial practice. The plants were grown in Elburn, Ill. in one-gallon containers in a glass-covered greenhouse for approximately 4 weeks and then outside for approximately 8 weeks. Greenhouse temperatures were maintained at approximately 60° F. to 65° F. (15.5° C. to 18.3° C.) during the day and approximately 55° F. to 60° F. (12.7° C. to 15.5° C.) during the night. No supplemental lighting was provided. Measurements and numerical values represent averages of typical plants.

Botanical classification: *Leucanthemum* x *superbum* 'White Magic'.

Parentage:

*Female parent*.—'Crazy Daisy', not patented.

*Male parent*.—Unknown.

Propagation:

*Type cutting*.—Terminal stem.

*Time to initiate roots*.—Approximately 10 to 12 days.

*Time to produce a rooted cutting*.—Approximately 35 to 42 days.

*Root description*.—Fibrous, thin, white to light brown in color.

*Rooting habit*.—Freely branching, dense.

Plant description:

*Commercial crop time*.—Approximately 10 to 12 weeks from a rooted cutting to finish in a 15 cm container.

*Growth habit and general appearance*.—Herbaceous perennial, moderately vigorous, upright growth habit.

*Hardiness*.—USDA Zone 5b to 9b.

*Size*.—Height from soil level to top of plant plane: Approximately 40.0 cm. Width: Approximately 55.0 cm.

*Branching habit*.—Freely branching. Quantity of lateral branches per plant: Approximately 11.

*Lateral branch*.—Strength: Strong. Length to base of peduncle: Approximately 25.0 cm. Diameter: Approximately 8.0 mm. Length of central internode: Approximately 2.7 cm. Texture: Densely pubescent. Color of young and mature stems: 146D.

Foliage description:

*General description*.—Quantity of leaves per lateral branch: Approximately 9. Fragrance: None detected. Form: Single. Arrangement: Alternate.

*Leaves*.—Aspect: Perpendicular to obtuse angle to stem. Shape: Oblanceolate. Margin: Serrate. Apex: Acute. Base: Sessile, truncate. Venation pattern: Pinnate. Length of mature leaf: Approximately 16.5 cm. Width of mature leaf: 3.5 cm. Texture of upper surface: Very slightly glossy, sparsely pubescent. Texture of lower surface: Moderately pubescent. Color of upper surface of young and mature foliage: 137A with midvein of 146C and other venation indistinguishable from leaf laminae. Color of lower surface of young and mature foliage: 137B with midvein of 146D and other venation indistinguishable from leaf laminae.

Flowering description:

*Flowering habit*.—'White Magic' is freely flowering under outdoor growing conditions with substantially continuous blooming from late spring through summer.

*Lastingness of individual inflorescence on the plant*.—Approximately 14 days.

Inflorescence description:

*General description*.—Type: Semi-double, composite, actinomorphic. Persistent. Shape: Round. Aspect: Erect. Arrangement: Terminal capitulum, positioned above the foliage. Quantity per plant: Approximately 36. Diameter: Approximately 7.5 cm to 8.0 cm. Depth: Approximately 2.0 cm. Fragrance: None detected.

*Peduncle*.—Strength: Strong. Aspect: Erect. Length: Approximately 20.5 cm. Diameter: Approximately 4.0 mm. Texture: Glabrous, slightly glossy. Color: 146B.

*Bud*.—Rate of opening: Generally takes 4 to 5 days for bud to progress from first color to fully open inflorescence. Quantity per plant: Approximately 25.

*Bud just before opening*.—Shape: Oblate. Diameter: Approximately 1.5 cm. Depth: Approximately 7.0 mm. Color: 145D.

*Ray florets*.—Quantity per inflorescence: Approximately 64. Arrangement: In a multiple whorls, imbricate. Aspect: Slightly concave. Shape: Narrowly elliptic. Margin: Entire. Apex: Two to three tips, acute to rounded. Base: Cuneate. Length: Approximately 2.3 cm to 3.5 cm. Width: Approximately 5.0 mm to 8.0 mm. Texture of upper and lower surfaces: Glabrous, axially ribbed. Color of upper surface when first and fully open: NN155D. Color of lower surface when first and fully open: NN155D.

*Disc florets*.—Quantity per inflorescence: Numerous, approximately 450. Arrangement: Massed in center of inflorescence. Shape: Tubular. Margin: Entire. Apex: Five acute tips. Base: Fused. Length: Approximately 8.0 mm. Diameter: Approximately 2.0 mm. Texture of outer surface: Slightly glossy, glabrous. Texture of inner surface: Glandular pubescent on tips. Color of upper or inner surface when first and fully open: 145C with tips of 13B and base of 145D. Color of lower or outer surface when fully open: 145C with tips of 13A and base of 145D.

*Disc*.—Diameter: Approximately 2.5 cm. Depth: Approximately 8.0 mm.

*Receptacle*.—Shape: Disc. Diameter: Approximately 1.8 mm. Color: 145D.

*Phyllaries*.—Quantity per inflorescence Approximately 36. Arrangement: In multiple whorls. Base of outer bracts fused into cup-shaped base, inner bracts surround receptacle, slightly imbricate, held close to ray florets.

*Outer phyllaries*.—Shape of free portion: Ovate. Margin: Entire. Apex: Acute. Base: Fused. Length: Approximately 9.0 mm. Width: Approximately 4.0 mm. Texture of upper surfaces: Glabrous, glossy. Texture of lower surfaces: Glabrous, matte. Color of upper and lower surfaces: 146B with papery transparent edges of 199D.

*Inner phyllaries*.—Shape: Lanceolate. Margin: Entire. Apex: Broadly acute. Base: Truncate. Length: Approximately 8.0 mm. Width: Approximately 2.0 mm. Texture of upper surfaces: Glabrous, glossy. Texture of lower surfaces: Glabrous, matte. Color of upper and lower surfaces: 146C with papery transparent edges of 199D.

*Reproductive organs*.—Androecium: Present on disc florets only. Stamen quantity: 5. Stamen length: Approximately 4.0 mm. Filament length: Approximately 2.0 mm. Filament color: Colorless, transparent. Anther shape: Oblong, basifixed. Anther length: Approximately 2.0 mm. Anther color: 23B. Pollen amount: Moderate to abundant. Pollen color: 23A. Gynoecium: Present on ray and disc florets. Pistil quantity: 1 per floret. Pistil length: Approximately 8.0 mm. Stigma shape: Bifid. Stigma length: Approximately 1.0 mm. Stigma color: 13B. Style length: Approximately 5.0 mm. Style color: 145C. Ovary length: Approximately 2.0 mm. Ovary color: 145D.

Seed and fruit production: Neither seed nor fruit production has been observed.

Disease and pest resistance: Resistance to pathogens and pests common to *Leucanthemum* has not been observed.

What is claimed is:

1. A new and distinct cultivar of *Leucanthemum* plant named 'White Magic', substantially as herein illustrated and described.

* * * * *